United States Patent
Yabu et al.

(10) Patent No.: US 11,078,381 B2
(45) Date of Patent: *Aug. 3, 2021

(54) CATECHOL-CONTAINING ADHESIVE HYDROGEL, COMPOSITION FOR PREPARING ADHESIVE HYDROGEL, AND COMPOSITIONS EACH INCLUDING SAID ADHESIVE HYDROGEL

(71) Applicant: Japan Science and Technology Agency, Saitama (JP)

(72) Inventors: Hiroshi Yabu, Sendai (JP); Matsuhiko Nishizawa, Sendai (JP); Kuniaki Nagamine, Sendai (JP); Yuta Saito, Sendai (JP); Jun Kamei, Sendai (JP); Tatsuaki Shimazaki, Sendai (JP); Shun Chihara, Sendai (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/801,309

(22) Filed: Feb. 26, 2020

(65) Prior Publication Data

US 2020/0190362 A1    Jun. 18, 2020

Related U.S. Application Data

(63) Continuation of application No. 15/575,869, filed as application No. PCT/JP2016/065634 on May 26, 2016, now Pat. No. 10,611,927.

(30) Foreign Application Priority Data

May 26, 2015    (JP) .................. 2015-106809

(51) Int. Cl.
   *C09J 4/00*       (2006.01)
   *C09D 4/00*       (2006.01)
   (Continued)

(52) U.S. Cl.
   CPC .................. *C09J 4/00* (2013.01); *A61K 6/30* (2020.01); *A61L 24/0031* (2013.01);
   (Continued)

(58) Field of Classification Search
   CPC ...... A61L 24/0031; A61L 24/06; A61L 26/00; A61L 26/0014; A61L 26/008;
   (Continued)

(56) References Cited

U.S. PATENT DOCUMENTS

2004/0097807 A1* 5/2004 Smith .................. A61B 8/4281
                                                         600/437
2009/0149084 A1* 6/2009 Meyer .................. H01R 4/4854
                                                         439/725

(Continued)

FOREIGN PATENT DOCUMENTS

JP      2003100349 A      4/2003
JP      2005034770 A      2/2005
   (Continued)

OTHER PUBLICATIONS

Skelton, S., Bostwick, M., O'Connor, K., Konst, S., Casey, S., Lee, B.P., "Biomimetic adhesive containing nanocomposite hydrogen with enhanced materials properties", Soft Matter, 2013, 9, 3825-3833 (Year: 2013).*

(Continued)

*Primary Examiner* — James C Goloboy
(74) *Attorney, Agent, or Firm* — Amster, Rothstein & Ebenstein LLP

(57) ABSTRACT

A hydrogel that adheres to the surface of materials is provided by using as constituent elements a water-soluble main chain monomer, crosslinking agent, polymerization initiator, and adhesive monomer having at least a catechol group in a side chain.

22 Claims, 2 Drawing Sheets

(51) Int. Cl.
- *C09D 5/16* (2006.01)
- *C10M 173/02* (2006.01)
- *C09D 7/40* (2018.01)
- *C10M 107/24* (2006.01)
- *A61L 26/00* (2006.01)
- *C09J 11/06* (2006.01)
- *C08F 220/58* (2006.01)
- *A61K 6/30* (2020.01)
- *A61L 24/00* (2006.01)
- *A61L 24/06* (2006.01)
- *C10M 107/22* (2006.01)

(52) U.S. Cl.
CPC ............. *A61L 24/06* (2013.01); *A61L 26/00* (2013.01); *A61L 26/008* (2013.01); *A61L 26/0014* (2013.01); *C08F 220/58* (2013.01); *C09D 4/00* (2013.01); *C09D 5/16* (2013.01); *C09D 7/40* (2018.01); *C09J 11/06* (2013.01); *C10M 107/22* (2013.01); *C10M 107/24* (2013.01); *C10M 173/02* (2013.01); *C10M 2217/024* (2013.01)

(58) Field of Classification Search
CPC . A61K 6/0023; C10M 107/22; C10M 107/24; C10M 173/02; C10M 2217/024; C09D 4/00; C09D 5/16; C09D 7/40; C09J 4/00; C09J 11/06; C08F 220/58
See application file for complete search history.

(56) References Cited

U.S. PATENT DOCUMENTS

| | | | |
|---|---|---|---|
| 2012/0156164 A1 | 6/2012 | Park et al. | |
| 2012/0329882 A1* | 12/2012 | Messersmith | A61L 27/18 514/772.1 |
| 2017/0156621 A1* | 6/2017 | Bettinger | A61L 27/52 |

FOREIGN PATENT DOCUMENTS

| | | | |
|---|---|---|---|
| JP | 2005034770 A | * | 10/2005 |
| JP | 2010501027 A | | 1/2010 |
| JP | 2013500072 A | | 1/2013 |
| JP | 2013503688 A | | 2/2013 |
| JP | 2014177636 A | | 9/2014 |
| WO | 2008019352 A1 | | 2/2008 |
| WO | 2009094060 A1 | | 7/2009 |
| WO | 2011011658 A1 | | 1/2011 |

OTHER PUBLICATIONS

Jpn J Artif Organs, vol. 22(2), 1993, pp. 394-397 with English Abstract.
Jpn J Artif Organs, vol. 24(1), 1995, pp. 74-78 with English Abstract.
Saito, Y. et al., Macromol. Rapid Commun., 2013, vol. 34, pp. 630-634.
PCT Written Opinion of the International Searching Authority dated Aug. 30, 2016 in connection with PCT International Patent Application No. PCT/JP2016/065634.
Communication Supplementary European Search Report dated May 15, 2018 in connection with European Patent Application No. 16800104.8.
Chung, H. et al., entitled "Enhanced Adhesion of Dopamine Methacrylamide Elastomers via Viscoelasticity Tuning," Biomacromolecules, vol. 12, Feb. 14, 2011, pp. 342-347.
Notification of Reasons of Refusal from the Japanese Patent Office dated Feb. 5, 2019 in connection with Japanese Patent Application No. 2017-520807.
Communication Pursuant to Article 94(3) EPC dated Jun. 21, 2019 in connection with European Patent Application No. 16800104.8.
Skelton et al., "Biomimetic Adhesive Containing Nanocomposite Hydrogen With Enhanced Materials Properties," Soft Matter, vol. 9, 2013, pp. 3825-3833. (Year: 2013).

* cited by examiner

CATECHOL-CONTAINING ADHESIVE HYDROGEL, COMPOSITION FOR PREPARING ADHESIVE HYDROGEL, AND COMPOSITIONS EACH INCLUDING SAID ADHESIVE HYDROGEL

CROSS-REFERENCE TO RELATED APPLICATIONS

This application is a continuation of U.S. patent application Ser. No. 15/575,869, filed Nov. 21, 2017, which is a U.S. national phase of PCT International Patent Application No. PCT/JP2016/065634, filed May 26, 2016, which claims priority to Japanese Patent Application No. 2015-106809, filed May 26, 2015, the contents of each of which are incorporated herein by reference in their entirety.

BACKGROUND OF THE INVENTION

1. Field of the Invention

The present invention relates to an adhesive hydrogel containing a catechol group, a composition for an adhesive hydrogel, an adhesive including a hydrogel, a bioadhesive, a medical adhesive, a ship bottom antifouling paint, a water-based lubricant, and a coating material for antifouling.

2. Description of the Related Art

A hydrogel is a three-dimensional network structure formed by crosslinking a polymer. Hydrogels are hydrous, endowed with flexibility, rich in absorbency, and present volume phase transition and are therefore utilized in various fields such as medical materials and industrial products. For example, various applications such as wound healing materials to adhere tissues, adhesives of implants, and matrices for drug delivery systems (DDS) are being studied as medical materials.

In recent years, imparting various functions to hydrogels in accordance with their purpose and applying them for the desired purpose have been studied. "Smart gels" in which the gel functions autonomously by sensing an outside stimulus such as heat, electricity, light, or pH are also being actively developed. Although hydrogels that have been imparted various functions in this way are being developed, their application is limited because hydrogels are endowed with virtually no adhesiveness to the surface of other materials such as metals.

The main reasons why hydrogels are not endowed with adhesiveness to the surface of other materials are that water is contained in the three-dimensional network of the crosslinked polymer of the hydrogel and the water content is high and that hydrogels are easily structurally deformed. Various attempts have therefore been made to impart adhesiveness to hydrogels. Methods of introducing photoinitiating groups such as phenylazide groups into a substrate and immobilizing a hydrogel, or affixing after having decomposed part of the gel by an excimer laser have been disclosed to date (Non-patent Documents 1 and 2).

A method of chemically modifying the polymer main chain and introducing an adhesive group has also been disclosed. Patent Document 1 discloses a bioinjectable tissue-adhesive hydrogel having tissue adhesive force through bonding with DOPA (3,4-dihydroxyphenylalanine) or a DOPA derivative. DOPA derivatives are adhesive materials discovered to adhere to the surface of various materials such as rocks, trees, metals, and concrete structures even in environments where mussels typified by common blue mussels are exposed to moist environments and severe tides. The catechol groups included in DOPA secreted from the byssus gland of mussels can adhere firmly to a variety of materials, even in water. Patent Document 1 prepares a hydrogel endowed with adhesiveness by linking a compound having a DOPA derivative to the main chain of a hydrogel.

Patent Document 2 discloses a method for producing a polymer gel endowed with adhesiveness by impregnating a base material porous film with a polymer having a polyacrylate structure or the like in the main chain and a chain-like oligoalkylene oxide structure in a side chain.

PRIOR ART DOCUMENTS

Patent Documents

[Patent Document 1] Published Japanese Translation of PCT Application No. 2013-503688
[Patent Document 2] JP Kokai 2003-100349

Non-Patent Documents

[Non-patent Document 1] Y. Nakayama, T. Matsuda, Jinko Zoki, 1993, Vol. 22(2), pp. 394-397.
[Non-patent Document 2] Y. Nakayama, T. Matsuda, Jinko Zoki, 1995, Vol. 24(1), pp. 74-78.
[Non-patent Document 3] Saito, Y. et al., Macromol. Rapid Commun., 2013, Vol. 34, pp. 630-634.

SUMMARY OF THE INVENTION

The method disclosed in Non-patent Document 1 requires chemical modification of the substrate surface and requires a complex procedure. The method disclosed in Non-patent Document 2 requires a strong light source. A hydrogel cannot be immobilized simply on a substrate surface even by using either method.

The method described in Patent Document 1 imparts adhesiveness to a hydrogel by introducing a strongly adhesive catechol group into the polymer main chain. However, all of the catechol groups introduced cannot be utilized in adhesion because the catechol groups introduced into the main chain are also used in linkage between polymers. Firm adhesive force was therefore not obtained. Moreover, there is a possibility that the hydrogel will fail to hold its shape in the presence of free catechol, and doubts remain about practical application. In addition, the purpose of the method of Patent Document 2 is not firm adhesion, as analyzed by the peeling adhesive strength in the examples, and the adhesiveness was inadequate. The purpose of the present invention is to provide a hydrogel endowed with firm enough adhesive force to be able to function even as an adhesive.

All of the catechol groups introduced function effectively as adhesible groups by causing the catechol groups, which are adhesive molecules, to be contained in a side chain rather than the main chain. The adhesive force can also be adjusted since the amount of catechol groups included in the side chain can be adjusted freely. However, there are problems such as the selection of the main chain monomer that polymerizes with the monomer containing a catechol group in a side chain and functions as a hydrogel and the fact that polymerization ceases because of a decline in the polarity of the catechol monomer due to imparting polymerizable groups; and it was difficult to realize a hydrogel that caused catechol groups to be contained in the side chain.

The purpose of the present invention is to provide a hydrogel that bonds firmly to the surface of various materials or to provide a variety of applications utilizing an adhesive hydrogel. The purpose is, by causing catechol groups to be contained in a side chain, to provide not only a hydrogel that can be adhered more firmly than conventional adhesive hydrogels but also to make it possible to provide a hydrogel having adjustable adhesive force and to provide a variety of applications.

The present invention relates to the following catechol-containing adhesive hydrogel, composition for preparing adhesive hydrogel, adhesive, medical adhesive, bioadhesive, ship bottom antifouling paint, water-based lubricant, and coating material for antifouling.

(1) An adhesive hydrogel having as constituent elements a water-soluble main chain monomer, a crosslinking agent, a polymerization initiator, and an adhesive monomer having a catechol group in a side chain.

(2) The adhesive hydrogel according to (1) wherein the catechol group is derived from DOPA or a derivative thereof.

(3) The adhesive hydrogel according to (1) or (2) wherein the water-soluble main chain monomer is a vinyl group-containing monomer.

(4) An adhesive hydrogel synthesized from a water-soluble main chain monomer, a crosslinking agent, a polymerization initiator, and an adhesive monomer having a catechol group in a side chain.

(5) The adhesive hydrogel according to (4) wherein the catechol group is derived from DOPA or a derivative thereof.

(6) The adhesive hydrogel according to (4) or (5) wherein the water-soluble main chain monomer is a vinyl group-containing monomer.

(7) The adhesive hydrogel according to any of (1)-(6) wherein at least one hydrogen of the catechol group is substituted by a substituent selected from a hydroxyl group, nitro group, carboxy group, and carbonyl group.

(8) The adhesive hydrogel according to any of (1)-(7) that also includes an electrolyte.

(9) A bioadhesive that includes the adhesive hydrogel according to (8).

(10) A composition for preparing adhesive hydrogel including a water-soluble main chain monomer, a crosslinking agent, a polymerization initiator, and an adhesive monomer having a catechol group in a side chain.

(11) The composition for preparing adhesive hydrogel according to (10) wherein the catechol group is derived from DOPA or a derivative thereof.

(12) The composition for preparing adhesive hydrogel according to (10) or (11) wherein the water-soluble main chain monomer is a vinyl group-containing monomer.

(13) The composition for preparing adhesive hydrogel according to any of (10)-(12) wherein at least one hydrogen of the catechol group is substituted by a substituent selected from a hydroxyl group, nitro group, carboxy group, and carbonyl group.

(14) The composition for preparing adhesive hydrogel according to any of (10)-(13) that also includes an electrolyte.

(15) An adhesive comprising a composition for preparing adhesive hydrogel according to any of (10)-(14).

(16) An adhesive containing a hydrogel wherein the adhesive according to (15) is used as a one-component adhesive where the water-soluble main chain monomer, crosslinking agent, polymerization initiator, and adhesive monomer are included in one component or as a two-component adhesive where the water-soluble main chain monomer, crosslinking agent, and adhesive monomer are included in a first component and the polymerization initiator is included in a second component.

(17) A medical adhesive wherein the adhesive according to (15) or (16) is used to adhere bone, teeth, or soft tissue or to adhere bone, teeth, or soft tissue and a medical member.

(18) The medical adhesive containing a hydrogel according to (17) wherein the medical member is a sensor electrode, stimulation electrode, or implant.

(19) A ship bottom antifouling paint containing a composition for preparing adhesive hydrogel according to any of (10)-(14).

(20) A water-based lubricant containing a composition for preparing adhesive hydrogel according to any of (10)-(14).

(21) A coating material for antifouling containing a composition for preparing adhesive hydrogel according to any of (10)-(14).

DESCRIPTION OF THE PREFERRED EMBODIMENTS

Figure 1:
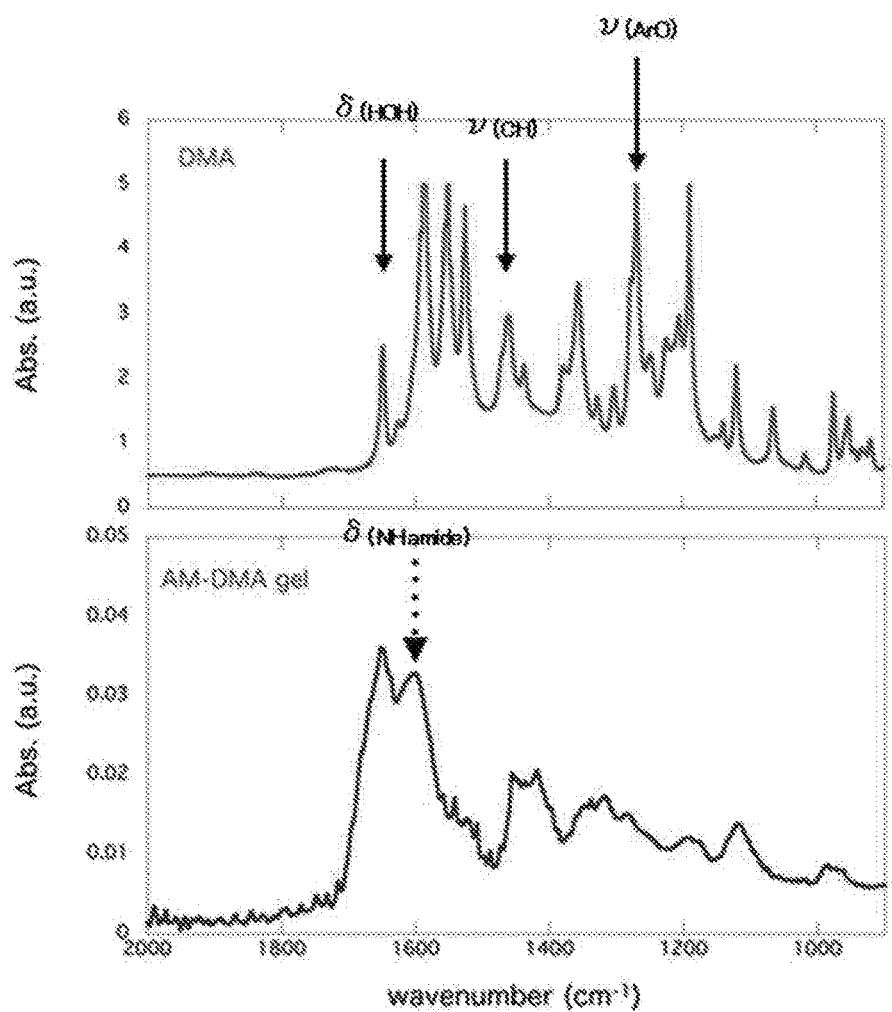
FIG. 1 is a drawing showing the FT-IR spectrum of a DMA monomer and the FT-IR ATR spectrum of a DMA-containing hydrogel.
Figure 1:
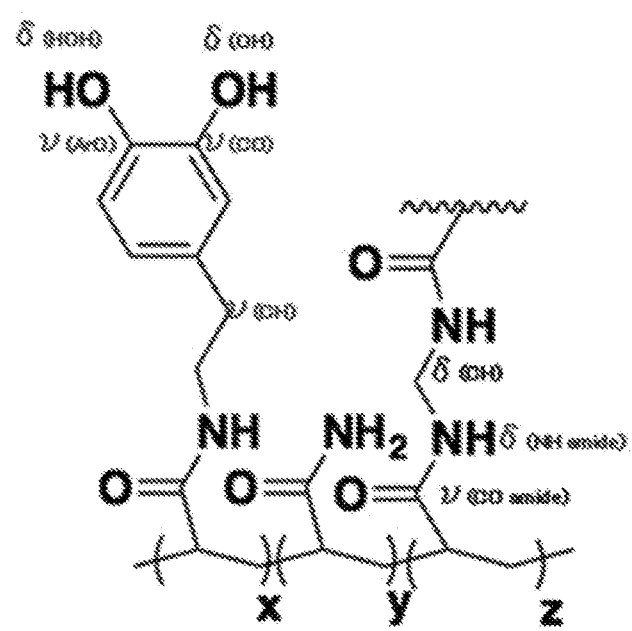

The adhesive monomer in the present invention is linked directly to the main chain, not through a catechol group of the side chain. Therefore, all of the catechol groups of the adhesive monomer can participate in adhesion to a substrate or the like. This makes it possible to prepare a hydrogel endowed with firm adhesiveness.

In the hydrogel of the present invention, any compound may be used as the main chain monomer as long as the compound is a water-soluble monomer. Water-soluble vinyl group-containing monomers, polyethylene glycol, and 2-hydroxyethyl methacrylate (HEMA) can be used appropriately. If the monomer is a water-soluble vinyl group-containing monomer, a water-soluble vinyl group-containing monomer of a structure represented by the following general formula (1) can preferably be used.

[Chemical formula 1]

(1)

In general formula (1), R1 represents a hydrogen, C1-20 linear, branched, or cyclic alkyl group, C6-20 aryl group, or C7-20 aralkyl group, preferably a hydrogen, C1-5 linear, branched, or cyclic alkyl group, more preferably a hydrogen or a C3 or lower linear alkyl group, even more preferably H or CH3.

R2 represents a C1-20 linear, branched, or cyclic alkyl group, C6-20 aryl group, or C7-20 aralkyl group, preferably a C1-8 linear, branched, or cyclic alkyl group, C6-8 aryl group, or C7 or 8 aralkyl group, more preferably a C3 or lower linear alkyl group.

X represents an amide group or ester group; it need not be included, but including an amide group or ester group is preferred.

When X is an amide or ester and R2 is a C1-20 linear, branched, or cyclic alkyl group, examples of the monomer represented by formula (1) include methyl (meth)acrylamide, ethyl (meth)acrylamide, n-propyl (meth)acrylamide, 2-propyl (meth)acrylamide, n-butyl (meth)acrylamide, 1-methylpropyl (meth)acrylamide, 2-methylpropyl (meth)acrylamide, tert-butyl (meth)acrylamide, n-pentyl (meth)acrylamide, 1-methylbutyl (meth)acrylamide, 1-ethylpropyl (meth)acrylamide, tert-pentyl (meth)acrylamide, 2-methylbutyl (meth)acrylamide, 3-methylbutyl (meth)acrylamide, 2,2-dimethylpropyl (meth)acrylamide, n-hexyl (meth)acrylamide, 1-methylpentyl (meth)acrylamide, 1-ethylbutyl (meth)acrylamide, 2-methylpentyl (meth)acrylamide, 3-methylpentyl (meth)acrylamide, 4-methylpentyl (meth)acrylamide, 2-methylpentan-3-yl (meth)acrylamide, 3,3-dimethylbutyl (meth)acrylamide, 2,2-dimethylbutyl (meth)acrylamide, 1,1-dimethylbutyl (meth)acrylamide, 1,2-dimethylbutyl (meth)acrylamide, 1,3-dimethylbutyl (meth)acrylamide, 2,3-dimethylbutyl (meth)acrylamide, 1-ethylbutyl (meth)acrylamide, 2-ethylbutyl (meth)acrylamide, heptyl (meth)acrylamide, octyl (meth)acrylamide, nonyl (meth)acrylamide, decyl (meth)acrylamide, undecyl (meth)acrylamide, dodecyl (meth)acrylamide, tridecyl (meth)acrylamide, tetradecyl (meth)acrylamide, pentadecyl (meth)acrylamide, hexadecyl (meth)acrylamide, heptadecyl (meth)acrylamide, octadecyl (meth)acrylamide, nonadecyl (meth)acrylamide, eicosyl (meth)acrylamide, cyclopropyl (meth)acrylamide, cyclobutyl (meth)acrylamide, cyclopentyl (meth)acrylamide, cyclohexyl (meth)acrylamide, and other such alkyl (meth)acrylamides; and methyl (meth)acrylate, ethyl (meth)acrylate, n-propyl (meth)acrylate, 2-propyl (meth)acrylate, n-butyl (meth)acrylate, 1-methylpropyl (meth)acrylate, 2-methylpropyl (meth)acrylate, tert-butyl (meth)acrylate, n-pentyl (meth)acrylate, 1-methylbutyl (meth)acrylate, 1-ethylpropyl (meth)acrylate, tert-pentyl (meth)acrylate, 2-methylbutyl (meth)acrylate, 3-methylbutyl (meth)acrylate, 2,2-dimethylpropyl (meth)acrylate, n-hexyl (meth)acrylate, 1-methylpentyl (meth)acrylate, 1-ethylbutyl (meth)acrylate, 2-methylpentyl (meth)acrylate, 3-methylpentyl (meth)acrylate, 4-methylpentyl (meth)acrylate, 2-methylpentan-3-yl (meth)acrylate, 3,3-dimethylbutyl (meth)acrylate, 2,2-dimethylbutyl (meth)acrylate, 1,1-dimethylbutyl (meth)acrylate, 1,2-dimethylbutyl (meth)acrylate, 1,3-dimethylbutyl (meth)acrylate, 2,3-dimethylbutyl (meth)acrylate, 1-ethylbutyl (meth)acrylate, 2-ethylbutyl (meth)acrylate, and other such alkyl (meth)acrylates.

When X is an amide or ester and R2 is a C6-20 aryl group, examples include phenyl (meth)acrylamide, indenyl (meth)acrylamide, pentalenyl (meth)acrylamide, naphthyl (meth)acrylamide, azulenyl (meth)acrylamide, fluorenyl (meth)acrylamide, and other such aryl (meth)acrylamides.

When X is an amide or ester and R2 is a C7-20 aralkyl group, examples include benzyl (meth)acrylamide and other such aralkyl (meth)acrylamides and benzyl (meth)acrylate and other such aralkyl (meth)acrylates.

On the other hand, examples of the monomer when X is not included in formula (1) and R2 is a C1-20 linear, branched, or cyclic alkyl group include propylene, 2-methyl-1-propylene, 1-butene, 2-methyl-1-butene, 3-methyl-1-butene, 3,3-dimethyl-1-butene, 3-methyl-2-ethyl-1-butene, 2,3-dimethyl-1-butene, 2-tert-butyl-3,3-dimethyl-1-butene, cyclopropylene, cyclobutene, cyclopentene, or cyclohexene.

Examples of the monomer when X is not included in formula (1) and R2 is a C6-20 aryl group include vinylbenzene (styrene) and other such vinyl aryls.

Examples of the monomer when X is not included in formula (1) and R2 is a C7-20 aralkyl group include 3-phenyl-1-propylene, 2-phenyl-1-propylene, 4-phenyl-1-butene, 3-phenyl-1-butene, 2-phenyl-1-butene, 5-phenyl-1-pentene, 4-phenyl-1-pentene, 3-phenyl-1-pentene, 2-phenyl-1-pentene, 6-phenyl-1-hexene, 5-phenyl-1-hexene, 4-phenyl-1-hexene, 3-phenyl-1-hexene, 2-phenyl-1-hexene, 7-phenyl-1-heptene, 6-phenyl-1-heptene, 5-phenyl-1-heptene, 4-phenyl-1-heptene, 3-phenyl-1-heptene, 2-phenyl-1-heptene, 8-phenyl-1-octene, 7-phenyl-1-octene, 6-phenyl-1-octene, 5-phenyl-1-octene, 4-phenyl-1-octene, 3 phenyl-1-octene, 2-phenyl-1-octene, 9-phenyl-1-nonene, 8 phenyl-1-nonene, 7-phenyl-1-nonene, 6-phenyl-1-nonene, 5 phenyl-1-nonene, 4-phenyl-1-nonene, 3-phenyl-1-nonene, 2 phenyl-1-nonene, 10-phenyl-1-decene, 9-phenyl-1-decene, 8-phenyl-1-decene, 7-phenyl-1-decene, 6-phenyl-1-decene, 5 phenyl-1-decene, 4-phenyl-1-decene, 3-phenyl-1-decene, 2 phenyl-1-decene, 11-phenyl-1-undecene, 10-phenyl-1-undecene, 9-phenyl-1-undecene, 8-phenyl-1-undecene, 7-phenyl-1-undecene, 6-phenyl-1-undecene, 5-phenyl-1-undecene, 4-phenyl-1-undecene, 3-phenyl-1-undecene, 2-phenyl-1-undecene, 12-phenyl-1-dodecene, 11-phenyl-1-dodecene, 10-phenyl-1-dodecene, 9-phenyl-1-dodecene, 8-phenyl-1-dodecene, 7-phenyl-1-dodecene, 6-phenyl-1-dodecene, 5-phenyl-1-dodecene, 4-phenyl-1-dodecene, 3-phenyl-1-dodecene, 2-phenyl-1-dodecene, 13-phenyl-1-tridecene, 12-phenyl-1-tridecene, 11-phenyl-1-tridecene, 10-phenyl-1-tridecene, 9-phenyl-1-tridecene, 8-phenyl-1-tridecene, 7-phenyl-1-tridecene, 6-phenyl-1-tridecene, 5-phenyl-1-tridecene, 4-phenyl-1-tridecene, 3-phenyl-1-tridecene, 2-phenyl-1-tridecene, 14-phenyl-1-tetradecene, 13-phenyl-1-tetradecene, 12-phenyl-1-tetradecene, 11-phenyl-1-tetradecene, 10-phenyl-1-tetradecene, 9-phenyl-1-tetradecene, 8-phenyl-1-tetradecene, 7-phenyl-1-tetradecene, 6-phenyl-1-tetradecene, 5-phenyl-1-tetradecene, 4-phenyl-1-tetradecene, 3-phenyl-1-tetradecene, 2-phenyl-1-tetradecene, and the like. In addition, these monomers may be used in combination with other organic monomers.

Crosslinking agents capable of introducing a three-dimensional crosslinked structure by polymerizable double bonds are broadly included as the crosslinking agent. Specific examples include N,N'-methylene bis(meth)acrylamide, N,N'-(1,2-dihydroxyethylene)-bis(meth)acrylamide, diethylene glycol di(meth)acrylate, (poly)ethylene glycol di(meth)acrylate, triethylene glycol di(meth)acrylate, propylene glycol di(meth)acrylate, trimethylolpropane di(meth)acrylate, trimethylolpropane tri(meth)acrylate, pentaerythritol di(meth)acrylate, pentaerythritol tri(meth)acrylate, pentaerythritol tetra(meth)acrylate, (poly) propylene glycol di(meth)acrylate, glycerin tri(meth)acrylate, glycerin acrylate methacrylate, ethylene oxide-modified trimethylolpropane tri(meth)acrylate, pentaerythritol tetra(meth)acrylate, dipentaerythritol hexa(meth)acrylate, and other such divinyl compounds; triallyl cyanurate, triallyl isocyanurate, triallyl phosphate, triallylamine, poly(meth)allyloxy alkane, (poly) ethylene glycol diglycidyl ether, glycerol diglycidyl ether, ethylene glycol, polyethylene glycol, propylene glycol, glycerin, pentaerythritol, ethylenediamine, polyethyleneimine, glycidyl (meth)acrylate, triallyl isocyanurate, trimethylolpropane di(meth)allyl ether, tetraallyloxyethane, glycerol propoxy triacrylate, and the like. These crosslinking agents can be used individually or in combinations of two or more types.

The adhesive polymer having a catechol group in the present invention can be produced by the method described in Non-patent Document 3. Here, an adhesive monomer containing a catechol group was prepared from methacrylic anhydride and dopamine hydrochloride, but adhesive monomers can be prepared by using water-soluble vinyl group-containing monomers the same as the main chain monomer in place of methacrylic anhydride. For example, compounds represented by the following general formula (2) can be used as the adhesive monomer.

[Chemical formula 2]

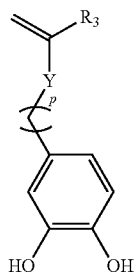

(2)

In general formula (2), R3 represents a hydrogen or C1-20 alkyl group; it may be linear, branched, or cyclic, and a hydrogen or C1-5 alkyl group is preferred. More preferred is a hydrogen or a C3 or lower linear alkyl group, even more preferred is H or CH3. Y represents an amide or ester, but need not be included. p represents 0 or an integer of 1-10, preferably 0 or an integer of 1-5, more preferably 0 or an integer of 1-3, even more preferably 2.

When Y is an amide, examples of such monomers include N-[2-(3,4-dihydroxyphenyl)methyl] (meth)acrylamide, N-[2-(3,4-dihydroxyphenyl)ethyl] (meth)acrylamide (sometimes referred to hereinafter as dopamine (meth)acrylamide, and sometimes abbreviated simply as DMA), N-[2-(3,4-dihydroxyphenyl)propyl] (meth)acrylamide, N-[2-(3,4-dihydroxyphenyl)butyl] (meth)acrylamide, N-[2-(3,4-dihydroxyphenyl)pentyl] (meth)acrylamide, N-[2-(3,4-dihydroxyphenyl)hexyl] (meth)acrylamide, N-[2-(3,4-dihydroxyphenyl)heptyl] (meth)acrylamide, N-[2-(3,4-dihydroxyphenyl)octyl] (meth)acrylamide, N-[2-(3,4-dihydroxyphenyl)nonyl] (meth)acrylamide, and N-[2-(3,4-dihydroxyphenyl)decyl] (meth)acrylamide.

When Y is an ester, examples include N-[2-(3,4-dihydroxyphenyl)methyl] (meth)acrylate, N-[2-(3,4-dihydroxyphenyl)ethyl] (meth)acrylate (sometimes referred to as dopamine (meth)acrylate), N-[2-(3,4-dihydroxyphenyl)propyl] (meth)acrylate, N-[2-(3,4-dihydroxyphenyl)butyl] (meth)acrylate, N-[2-(3,4-dihydroxyphenyl)pentyl] (meth)acrylate, N-[2-(3,4-dihydroxyphenyl)hexyl] (meth)acrylate, N-[2-(3,4-dihydroxyphenyl)heptyl] (meth)acrylate, N-[2-(3,4-dihydroxyphenyl)octyl] (meth)acrylate, N-[2-(3,4-dihydroxyphenyl)nonyl] (meth)acrylate, and N-[2-(3,4-dihydroxyphenyl)decyl] (meth)acrylate.

When Y is not included, examples include 3,4-dihydroxystyrene, 3-(3,4-dihydroxyphenyl)-1-propene, 4-(3,4-dihydroxyphenyl)-1-butene, 5-(3,4-dihydroxyphenyl)-1-pentene, 6-(3,4-dihydroxyphenyl)-1-hexene, 7-(3,4-dihydroxyphenyl)-1-heptene, 8-(3,4-dihydroxyphenyl)-1-octene, 9-(3,4-dihydroxyphenyl)-1-nonene, 10-(3,4-dihydroxyphenyl)-1-decene, 3-(3,4-dihydroxyphenyl)-2-methyl-1-propene, 4-(3,4-dihydroxyphenyl)-2-methyl-1-butene, 5-(3,4-dihydroxyphenyl)-2-methyl-1-pentene, 6-(3,4-dihydroxyphenyl)-2-methyl-1-hexene, 7-(3,4-dihydroxyphenyl)-2-methyl-1-heptene, 8-(3,4-dihydroxyphenyl)-2-methyl-1-octene, 9-(3,4-dihydroxyphenyl)-2-methyl-1-nonene, and 10-(3,4-dihydroxyphenyl)-2-methyl-1-decene.

The adhesiveness of the hydrogel is proportionate to the number of catechol groups contained in the hydrogel. Therefore, when firm adhesiveness is required, one may increase the amount of adhesive monomer including catechol groups in the side chain. In other words, the desired adhesive strength can be obtained by adjusting the amount of adhesive monomer.

One or more substituents may be introduced at R4-R6 in the following general formula (3) as an adhesive monomer for imparting adhesiveness in the present invention. In other words, the side chain may include a group in which a hydrogen of the catechol group has been substituted by a substituent. A hydroxyl group, nitro group, carboxy group, carbonyl group, or the like can be contained as a substituent. When substituents are introduced, the same groups may be introduced or different groups may be introduced. Introducing substituents at R4-R6 can weaken the adhesiveness in comparison to when the side chain is made from catechol groups. When firm adhesiveness is not required, the strength of adhesiveness can be adjusted not only by adjusting the amount of adhesive monomer but also by using an adhesive monomer in which substituents such as a hydroxyl group, nitro group, carboxy group, or carbonyl group have been introduced.

[Chemical formula 3]

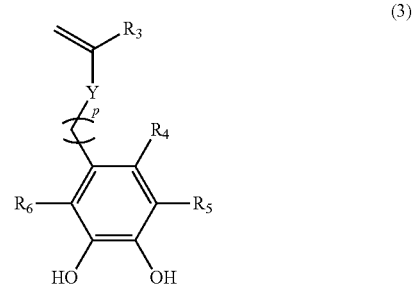

(3)

One derived from DOPA or a derivative thereof is preferred as the adhesive monomer having a catechol group used in the present invention for performance and ease of production. One derived from DOPA is more preferred in terms of ease of availability. Here, one derived from DOPA or a derivative thereof means one represented by p=2 among those represented by the above general formula (2) or (3), and one derived from DOPA is preferred for the ease of production. Specifically, this means one that can be synthesized form DOPA (3,4-dihydroxyphenylalanine), more preferably dopamine (meth)acrylamide or dopamine (meth)acrylate. Dopamine (meth)acrylamide is more preferred for the ease of production.

The adhesive monomer having a catechol group may be added in a proportion of usually 1% or more, preferably 3% or more, more preferably 5% or more, even more preferably 8% or more, and usually 50% or less, preferably 30% or less, more preferably 20% or less, and even more preferably 15% or less, relative to the total number of mol of main chain monomer and adhesive monomer.

Any such as a photopolymerization initiator, thermal polymerization initiator, or the like may be used as the polymerization initiator, but a photopolymerization initiator is preferably used. The photopolymerization initiator is not particularly restricted as long as it is cleaved by ultraviolet rays or visible light rays to generate radicals. Examples include 2,2'-azobis-N-(2-hydroxyethyl)propionamide, 2,2'- azobis(1-imino-1-pyrrolidino-2-methylpropane)dihydrochloride, and other such azo polymerization initiators; α-hydroxyketone, α-aminoketone, benzyl methyl ketal, bisacylphosphine oxide, metallocene, and the like; more specifically, 1-[4-(2-hydroxyethoxy)-phenyl]-2-hydroxy-2-methyl-propan-1-one (product name: IRGACURE (registered trade mark) 2959, manufactured by BASF Japan), 2-hydroxy-2-methyl-1-phenyl-propan-1-one (product name: Darocur (registered trade mark) 1173, manufactured by BASF Japan), 1-hydroxy-cyclohexyl-phenyl-ketone (product name: IRGACURE (registered trade mark) 184, manufactured by BASF Japan), 2-methyl-1-[(methylthio)phenyl]-2-morpholinopropan-1-one (product name: IRGACURE (registered trade mark) 907, manufactured by BASF Japan), 2-benzyl-2-dimethylamino-1-(4-morpholinophenyl)-butan-1-one (product name: IRGACURE (registered trade mark) 369, manufactured by BASF Japan), and the like. These photopolymerization initiators may be used individually or in combinations of two or more types.

The adhesive hydrogel of the present invention can be obtained by polymerizing the above constituent elements. Specifically, a composition including the water-soluble main chain monomer, crosslinking agent, and adhesive monomer containing a catechol group in a side chain (hereinafter, composition for hydrogel production) can be prepared and polymerized.

The polymerization method is not particularly restricted as long as a structure having the adhesive monomer including a catechol group as a side chain is obtained relative to the water-soluble main chain monomer.

The method of polymerization is not particularly restricted, and commonly used polymerization methods are used. However, solution polymerization is preferred. The adhesive hydrogel of the present invention is usually polymerized by dissolving the constituent elements in a solution including water. Other polar solvents can be used in combination as long as they do not inhibit the performance of the adhesive hydrogel or the polymerization reaction. The use of other polar solvents can improve the solubility of the water-soluble main chain monomer and adhesive monomer. The concentration of the reaction solution when these monomer components have been dissolved is not particularly restricted, but 0.1 M or higher is preferred.

The polar solvent is not particularly restricted. Specifically, dimethylsulfoxide (DMSO), methanol, N-methylpyrrolidone (NMP), ionic liquids, and the like can be used; DMSO is preferred for copolymerizing an adequate amount of adhesive monomer.

The hydrogel obtained by the polymerization reaction has strong adhesiveness. Although the structure is not particularly restricted, the hydrogel has a structure in which the water-soluble monomer has been polymerized as the main chain and the adhesive monomer having a catechol group has been polymerized as a side chain. The mode of polymerization is not particularly restricted, but the hydrogel is usually a random copolymer. Among structures having an adhesive monomer, specifically when the adhesive monomer is a vinyl group-containing monomer, the vinyl groups serve as crosslinking points and form bonds with the crosslinking agent. On the other hand, the hydrogel has a structure in which catechol groups are present in the polymer in a free state. The catechol groups function as adhesible points and actualize the function of an adhesive hydrogel.

The pH of the hydrogel of the present invention is not particularly restricted, but is usually 10 or lower, preferably 9 or lower. This is because adequate adhesiveness can be obtained by a pH within this range since hydrogen bonding capacity is not inhibited.

The hydrogel of the present invention can be used as a one-component adhesive or a two-component adhesive. When used as a one-component adhesive, the water-soluble main chain monomer, crosslinking agent, polymerization initiator, and adhesive monomer (composition for hydrogel production) may be contained in one component. When used as a two-component adhesive, the water-soluble main chain monomer, crosslinking agent, and adhesive monomer may be included in a first component and the polymerization initiator in a second component.

Thickening agents, surfactants, antioxidants, light resistance stabilizers, defoaming agents, plasticizers, pigments, and other such coloring agents may also be added as needed to improve the process suitability and adhesiveness of these adhesives. Other aqueous dispersions, for example, vinyl acetate-based, ethylene-vinyl acetate-based, acrylic, acrylic-styrene-based, and other such emulsions; styrene-butadiene-based, acrylonitrile-butadiene-based, acrylic-butadiene-based, and other such latexes; polyethylene-based, polyolefin-based, and other such ionomers; polyurethane, polyester, polyamide, epoxy-based resins, and the like may also be admixed within the range that does not harm the effects of the present invention.

The adhesive of the present invention can firmly adhere the hydrogel to the surface of various materials. For example, it has adhesiveness to inorganic materials such as hydroxyapatite, titanium oxide, zinc oxide, iron oxide, and glass, metals such as iron, gold, silver, and titanium, and resins such as polytetrafluoroethylene (PTFE) and polyimide. Hydrogels of different compositions can also be adhered to a substrate by utilizing the adhesiveness to the surfaces of these materials. Applications such as the following are therefore possible.

An adhesive made from the hydrogel composition of the present invention can be used as a medical adhesive to adhere bone, teeth, or soft tissue or to adhere bone, teeth, or soft tissue and a medical device. The adhesive can be used as a hard tissue adhesive to adhere hard tissues such as bones and teeth. For example, the adhesive can be used bone and artificial bone in a surgical procedure, and repair broken teeth and in adhesive bridges in the dental field. It can also be used for wound adhesion and surgical anastomoses as an adhesive of the skin, gastrointestinal tract, blood vessels, trachea, and other such soft tissues.

Furthermore, the adhesive can be used to adhere these tissues and a sensor electrode, stimulation electrode, implant, or other such medical member. Since the hydrogel endowed with adhesiveness of the present invention is endowed with firm adhesiveness, it is suitable for use as a wearable device for attaching a sensor electrode or stimulation electrode to the body for health management, diagnosis, or treatment. It can also be used as a suitable adhesive for immobilizing dental and bone implants. Pigments, drugs, and other such optional additives may be added as needed when used as a medical adhesive.

The adhesive hydrogel of the present invention can also be used as a coating material for antifouling to prevent proteins and cells from adhering to implantable medical devices such as catheters, stents, and cardiac pacemakers. For example, urinary tract infections triggered by microorganisms forming colonies in catheters are a problem as a frequent nosocomial infection. The adhesion of microorganisms to these medical devices can be prevented by coating them with hydrogel. Known pigments, antimicrobials, and other such optional additives may be added as needed when the adhesive hydrogel of the present invention is used as a coating material for antifouling.

Furthermore, the adhesive hydrogel of the present invention can also be used as a peelable adhesive by using one with weakened adhesiveness by decreasing the content of catechol groups or by substituents such as nitro groups or hydroxyl groups. The adhesive becomes peelable by weakening the adhesiveness, and it can be used suitably as a bioadhesive since it can be used repeatedly. It can also be used as an electrode used by affixing an EMS (electrical muscle stimulation) or other such health device electrode, ECG electrode, low frequency treatment device electrode, or the like to the skin by adding an electrolyte to the hydrogel. The following electrolytes may be contained in the aqueous solution when preparing the hydrogel when the bioadhesive is used as an electrode.

Any compound may be used as an electrolyte as long as it generates cations and anions in aqueous solution. Those that generate a sodium ion, potassium ion, magnesium ion, calcium ion, chloride ion, phosphate ion, and other such electrolyte ions can preferably be used. Specifically, a sodium halide such as sodium chloride, potassium halide, magnesium halide, calcium halide, or other such alkali metal halide, alkaline earth metal halide, or the like may be contained in the aqueous solution. Salts of an inorganic acid such as hypochlorous acid, sulfuric acid, and phosphoric acid and various metals, ammonium salts of these inorganic acids, various metal salts and ammonium salts of monocarboxylic acids such as acetic acid, benzoic acid, and lactic acid, salts of one or more metals or ammonia and polycarboxylic acids such as phthalic acid, succinic acid, adipic acid, citric acid, and tartaric acid, and the like can also be used. These electrolytes may be used individually, or configured so that two or more types are contained in the aqueous solution during production of the hydrogel. They may also be used by immersing the hydrogel in an aqueous solution containing the electrolyte after hydrogel production to substitute the water in the hydrogel by electrolyte solution.

The hydrogel of the present invention can also be made to include an electrolyte and used to affix an electrode to a building or the like. For example, the hydrogel of the present invention can be used when adhering an electrode to a bridge of the like. Since an electrolyte is included, an electric current can be applied by pasting an electrode to a building such as a bridge. The adhesiveness is good and adhesion is simple since the hydrogel adheres well even if rust forms. The same electrolytes as the above may be added as the electrolyte when pasting an electrode to a building.

The adhesive hydrogel of the present invention can also be used as a ship bottom antifouling paint. The common method for preventing biofouling is to fix an antifouling polymer to the surface. Since the hydrogel of the present invention can adhere firmly to metals such as iron, the ship's bottom can be coated with hydrogel. Coating the bottom of the ship by hydrogel can prevent sea creatures such as barnacles from adhering to the bottom of the ship. Organic antifouling components, plasticizers, inorganic dehydrating agents (stabilizers), antisagging agents, antisettling agents, coloring pigments, rust inhibitors, and the like may be added as needed when the adhesive hydrogel of the present invention is used as a ship bottom antifouling paint.

The composition for preparing adhesive hydrogel of the present invention can also be used suitably as a water-based lubricant. If a hydrogel with high biocompatibility is used, it can be used as a lubricant between an implant and a bone or even as a lubricant for machine parts that use a water-based lubricant such as in cutting. A water-based lubricant of the present invention may contain components known as constituent components of lubricant compositions, such as rust inhibitors, binders, defoaming agents, foaming agents, emulsifiers, preservatives, and the like, as needed.

The adhesive hydrogel of the present invention can be used without modification as a coating material for antifouling, ship bottom antifouling paint, and water-based lubricant by coating a base material. A base material can also be coated by the adhesive hydrogel and a non-adhesive hydrogel coated on top of that, for use as a coating material for antifouling and the like.

Example 1

<<Production of Adhesive Hydrogel>>

A prepolymer aqueous solution was adjusted using 950 mM of acrylamide as water-soluble main chain monomer, 13.0 mM of N,N-methylenebisacrylamide as crosslinking agent, 65.6 mM of 2-hydroxy-2-methylpropiophenone as polymerization initiator, and 50 mM of dopamine methacrylamide (DMA) as adhesive monomer. An aqueous solution obtained by adding DMSO to make 3.3 mL to 6.7 mL of PBS (2.68 mM KCl, 136.9 mM NaCl, 8.05 mM $Na_2HPO_4$, 1.47 mM $KH_2PO_4$) was used as the solvent. The adjusted prepolymer aqueous solution was nitrogen bubbled for two minutes to remove oxygen which inhibits polymerization. Adding DMSO to the aqueous solution permits polymerization even if the polarity of the catechol groups to which polymerizable groups have been imparted decreases.

The prepolymer aqueous solution was cast on a UV-permeable acrylic plate, irradiated for six hours with 1 $mW/cm^2$ of light having a wavelength of 300 nm in a nitrogen atmosphere, and a polymerized hydrogel was synthesized. The composition of the hydrogel obtained was confirmed by Fourier transform infrared attenuated total reflectance (FT-IR ATR) using an FT/IR6100 (manufactured by Jasco).

FIG. 1 shows the results of FT-IR ATR analysis of the DMA monomer and the hydrogel including DMA. A stretching vibration from the amide of the acrylamide (shown by the dotted arrow in the drawing) and a peak from the catechol group (shown by the solid arrow in the drawing) were obtained. DMA was introduced as a side chain in the gel mixed with DMA, and DMA was confirmed to be present on the gel surface.

Example 2

<<Study of Hydrogel Adhesiveness>>

A prepolymer aqueous solution was adjusted by varying the DMA concentration from 0 to 200 mM so that the sum with acrylamide would be 1000 mM. Table 1 shows the composition of the aqueous solution. A quantity of 30 µL of the prepared solution was placed between two slide glasses so that the adhered surface would be 20 mm×26 mm, irradiated for six hours by 1 $mW/cm^2$ of light having a wavelength of 300 nm in a nitrogen atmosphere, and polymerized.

TABLE 1

| Sample | 1 | 2 | 3 | 4 |
|---|---|---|---|---|
| DMA | 0 mM | 50 mM | 100 mM | 200 mM |
| Acrylamide | 1000 mM | 950 mM | 900 mM | 800 mM |
| N,N'-methylenebisacrylamide | | 13.0 mM | | |
| 2-Hydroxy-2-methylpropiophenone | | 65.6 mM | | |
| Solvent | | PBS (6.7 mL) + DMSO (3.3 mL) | | |

A lap shear test was conducted using the samples prepared. The hydrogel obtained was set in a tensile tester (manufactured by Imada Co., Ltd., DPU), pulled at a rate of 10 mm/min, and the peeling stress of the hydrogel was measured by a lap shear test. Each lap shear test was conducted three times, and the average value was calculated as the peeling stress.

Lap shear tests were conducted on a DMA-free hydrogel sample 1 and hydrogel samples 2, 3, and 4 including the concentrations of DMA shown in Table 1. While the peeling stress of sample 1 was 0.93 kPa, that of sample 2 (DMA concentration 50 mM) was 14.9 kPa, that of sample 3 (DMA concentration 100 mM) was 31.8 kPa, and that of sample 4 (DMA concentration 200 mM) was 13.9 kPa.

Sample 3 was able to obtain strength at least 30 times greater than the DMA-free sample 1. Adhesive force greater than sample 3 was not obtained even at the maximum DMA content of 200 mM. This is thought to be because the pH decreases rapidly (pH 5 and below) as the DMA content increases and inhibits the hydrogen bonding capacity. A hydrogel with higher adhesiveness can also be prepared by adjusting the pH, but the content of adhesive monomer is preferably 50% or less relative to the total number of moles of main chain monomer and adhesive monomer in consideration of the water solubility of the catechol groups.

Example 3

<<Study of Hydrogel Adhesiveness to Different Base Materials>>

Acrylamide (60 mg/mL), DMA (20 mg/mL), N,N-methylenebisacrylamide (20 mg/mL), and IRGACURE 2959 (10 µg/mL) were dissolved in 6.7 mL of PBS buffer (pH 7) and 3.3 mL of DMSO, cast on glass and metal substrates, the surface of which had been cleaned by oxygen plasma (100 W, for one minute), collagen gel, soft contact lens, and Teflon (registered trade mark) substrates, and photopolymerized under the same conditions as in Example 1.

When it was checked whether the hydrogel could be pulled off with tweezers, the hydrogel adhered stably without peeling in all cases except the Teflon substrate. This result confirmed that DMA-containing hydrogel can be peeled from a Teflon substrate and adheres firmly to other substrates. Although the results are not shown here, the hydrogel could also adhere to base materials such as silver, titanium, titanium oxide, iron oxide, and zinc oxide endowed with similar surface characteristics.

Example 4

<<DMA-Containing Hydrogel Formation on Hydrogel Surface>>

Formation of a DMA-containing hydrogel on the surface of a double network (sometimes abbreviated hereinafter as DN) gel was attempted. DN gel was synthesized by the following method. Sodium 2-acrylamide-2-methyl-1-propanesulfonate, N,N'-methylenebisacrylamide, and 2-oxoglutaric acid were prepared in respective concentrations of 1 M, 40 mM, and 1 mM. The solution was placed between glass plates, and an initial gel was synthesized by polymerizing for six hours in a nitrogen atmosphere while irradiating with UV light at an intensity of 1 mW/cm$^2$. Thereafter, dimethylacrylamide, N,N'-methylenebisacrylamide, and 2-oxoglutaric acid were each prepared in concentrations of 3 M, 3 mM, and 3 mM, the gel was soaked for two nights and polymerized in the same way to synthesize a DN gel.

A quantity of 50 III, of the prepolymer solution of DMA shown in sample 4 of Example 2 was cast on a Teflon substrate, and 15 mm$^2$ of the 0.5 mm thick DN gel synthesized was placed on it. Photopolymerization was conducted thereafter for 20 minutes under the same conditions as in Example 2, and the sample was gelled. The hydrogel obtained was peeled from the Teflon substrate, and the composition of the air side and Teflon substrate side of the gel was measured by FT-IR-ATR.

Figure 2:
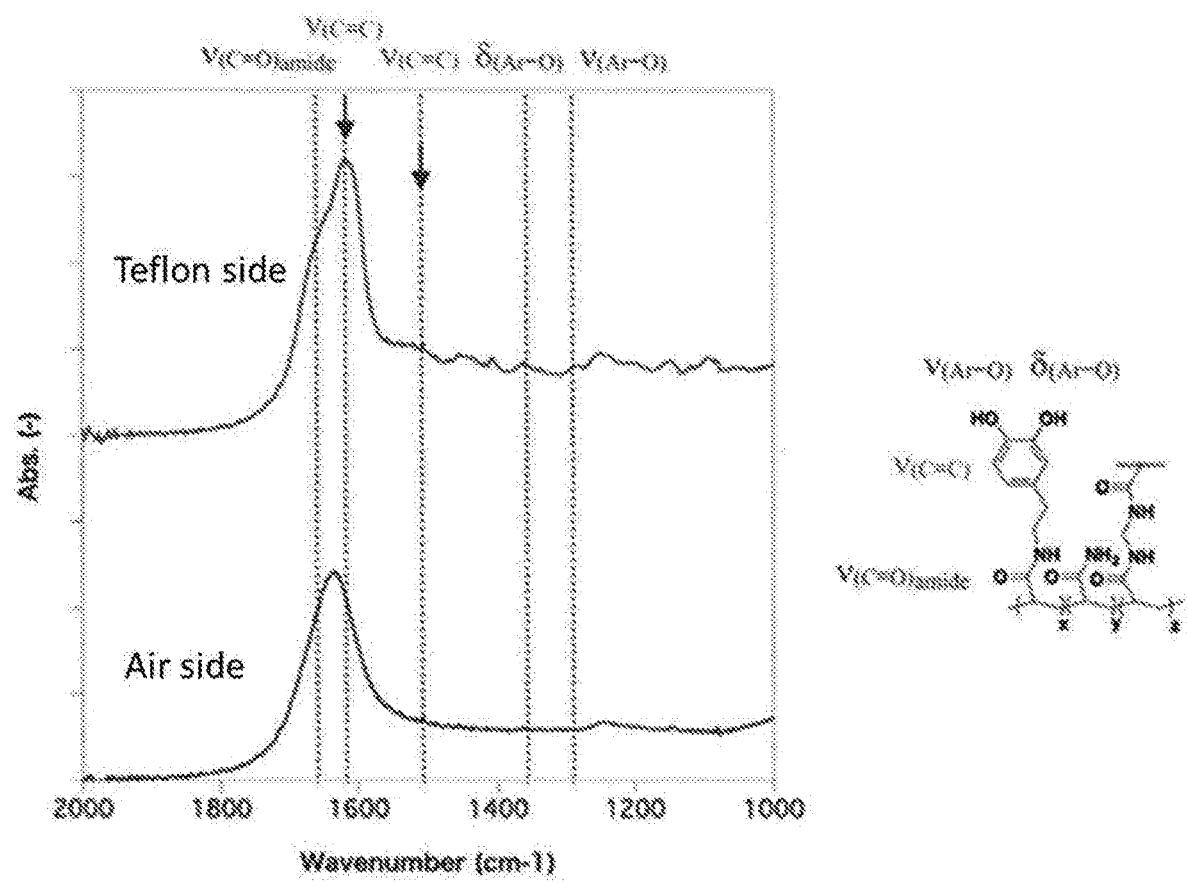
FIG. 2 is a drawing showing the FT-IR ATR spectrum of a double network gel.

FIG. 2 shows the FT-IR-ATR spectra of the side facing the Teflon (Teflon side), which was the substrate, and the side facing the air (air side). While only a strong peak from the amide of acrylamide was observed on the air side, an absorption peak (shown by an arrow in the drawing) from DMA was observed on the Teflon side. As shown in FIG. 2, a DMA-containing hydrogel can be formed on a specific surface of a hydrogel. In other words, it is possible to form an adhesive DMA-containing hydrogel on the substrate side and to position a non-adhesive hydrogel on the surface. This permits applications such as covering the surface of implants and artificial joints that require lubricity by hydrogel and preventing barnacles and other such organisms from adhering by coating ship bottoms with hydrogel.

INDUSTRIAL APPLICABILITY

The adhesive hydrogel of the present invention is endowed with firm adhesiveness and can be utilized in adhesives and hydrogel coating because it can bond to various base materials. Specifically, it can be utilized as a medical adhesive, coating material for antifouling, ship bottom antifouling paint, and water-based lubricant. When the adhesive hydrogel of the present invention is used as a coating material for antifouling, ship bottom antifouling paint, or water-based lubricant, the base material may be used as is coated by adhesive hydrogel or with the base material coated by adhesive hydrogel and also coated by hydrogel.

What is claimed is:

1. A composition for preparing adhesive hydrogel including a water-soluble main chain monomer, a crosslinking agent, a polymerization initiator, an adhesive monomer having a catechol group in a side chain, and water, provided that any inorganic nano-silicate in not included.

2. The composition for preparing adhesive hydrogel according to claim 1, wherein the adhesive monomer is added in a proportion of 8% or more to the total number of mol of the main chain monomer and the adhesive monomer.

3. The composition for preparing adhesive hydrogel according to claim 1, wherein the catechol group is derived from DOPA or a derivative thereof.

4. The composition for preparing adhesive hydrogel according to claim 1, wherein the water-soluble main chain monomer is a vinyl group-containing monomer.

5. The composition for preparing adhesive hydrogel according to claim 1, further comprising an electrolyte and/or a polar solvent.

6. The composition for preparing adhesive hydrogel according to claim 1, wherein the crosslinking agent is a crosslinking agent capable of introducing a three-dimensional crosslinked structure by polymerizable double bonds.

7. A method of applying an amount of the composition of claim 1 onto a ship bottom effective to antifoul paint.

8. A method of coating a base material with an amount of the composition of claim 1 effective to lubricate the top of the base material.

9. A method of applying an amount of the composition of claim 1 onto a base material effective to antifoul the base material.

10. A method for synthesizing an adhesive hydrogel including (i) a step of preparing a prepolymer aqueous solution containing a composition of claim 1, and (ii) a polymerization initiation step for conducting a polymerization initiation reaction in the prepolymer aqueous solution.

11. The composition for preparing adhesive hydrogel according to claim 1, substantially composed of a water-soluble main chain monomer, a crosslinking agent, a polymerization initiator, an adhesive monomer having a catechol group in a side chain, agents which are used to make buffer action in the adhesive hydrogel and water, and wherein the adhesive monomer is added in a proportion of 5% or more to the total number of mol of the main chain monomer and the adhesive monomer.

12. The composition for preparing adhesive hydrogel according to claim 11, wherein the adhesive monomer is added in a proportion of 8% or more to the total number of mol of the main chain monomer and the adhesive monomer.

13. The composition for preparing adhesive hydrogel according to claim 11, wherein the catechol group is derived from DOPA or a derivative thereof.

14. The composition for preparing adhesive hydrogel according to claim 11, wherein the water-soluble main chain monomer is a vinyl group-containing monomer.

15. The composition for preparing adhesive hydrogel according to claim 11, further comprising an electrolyte and/or a polar solvent.

16. The composition for preparing adhesive hydrogel according to claim 11, wherein the crosslinking agent is a crosslinking agent capable of introducing a three-dimensional crosslinked structure by polymerizable double bonds.

17. A method of applying an amount of the composition of claim 11 onto a ship bottom effective to antifoul paint.

18. A method of coating a base material with an amount of the composition of claim 11 effective to lubricate the top of the base material.

19. A method of applying an amount of the composition of claim 11 onto a base material effective to antifoul the base material.

20. A method for synthesizing an adhesive hydrogel including (i) a step of preparing a prepolymer aqueous solution containing a composition of claim 11, and (ii) a polymerization initiation step for conducting a polymerization initiation reaction in the prepolymer aqueous solution.

21. A method of (i) adhering bone, teeth, or soft tissues, or (ii) of adhering bone, teeth, or soft tissue and a medical member, with an adhesive in a medical field, the adhesive comprising a composition for preparing adhesive hydrogel including:

a water-soluble main chain monomer, a crosslinking agent, a polymerization initiator, an adhesive monomer having a catechol group in a side chain, and water, wherein the adhesive monomer is added in a proportion of 5% or more to the total number of mol of the main chain monomer and the adhesive monomer, and wherein all of the catechol groups of the adhesive monomer can participate in adhesion to a substrate and the hydrogel has a structure in which the catechol groups are present in the polymer in a free state.

22. The method of adhering according to claim 21, wherein the medical member is a sensor electrode, a stimulation electrode, or an implant.

* * * * *